United States Patent [19]
Belt et al.

[11] Patent Number: 5,057,285
[45] Date of Patent: * Oct. 15, 1991

[54] GAS GENERATOR/INDICATOR UNIT ADAPTED FOR USE IN AN UPRIGHT POSITION

[75] Inventors: William E. Belt, Kansas City, Mo.; C. Frederick Avery, Rockford, Ill.; Vernon W. Klein, Kansas City, Mo.

[73] Assignee: Marion Laboratories, Inc., Kansas City, Mo.

[ * ] Notice: The portion of the term of this patent subsequent to Feb. 17, 2004 has been disclaimed.

[21] Appl. No.: 23,763

[22] Filed: Mar. 9, 1987

[51] Int. Cl.$^5$ ................................................. B01J 7/00
[52] U.S. Cl. ...................................... 422/236; 422/58; 422/238; 422/239; 423/219; 435/299
[58] Field of Search ..................... 422/58, 61, 94, 236, 422/238, 239; 423/219; 435/299; 55/414, 444

[56] References Cited

U.S. PATENT DOCUMENTS

| | | | |
|---|---|---|---|
| 2,474,540 | 6/1949 | Marsh | 55/444 |
| 3,689,224 | 9/1972 | Agnew et al. | 422/61 |
| 4,013,422 | 3/1977 | Spinner et al. | 422/61 |
| 4,347,222 | 8/1982 | Beall et al. | 422/236 |
| 4,377,554 | 3/1983 | Johnson | 422/236 |
| 4,605,617 | 8/1986 | Kasugai | 422/61 |
| 4,643,973 | 2/1987 | Avery | 422/236 |

*Primary Examiner*—Robert J. Warden
*Assistant Examiner*—Timothy M. McMahon

[57] ABSTRACT

A unit in the form of a bubble pack for creating an anaerobic gaseous atmosphere in an upright container and for indicating the presence of the anaerobic atmosphere in the container. One bubble of the pack houses acid-containing ampoules while another bubble houses a tablet which generates hydrogen and carbon dioxide when activated by squeezing the first bubble to crush the ampoules and release the acid. Gas flows from the second bubble, through the first bubble and then into the container and enters still another bubble which houses an ampoule containing a redox color indicating liquid. When the latter ampoule is crushed, the liquid moistens an absorbent pad which changes colors as the atmosphere of the container changes from aerobic to anaerobic. The pack also carries catalyst pellets to promote a reaction between the generated hydrogen and the oxygen in the container.

4 Claims, 2 Drawing Sheets

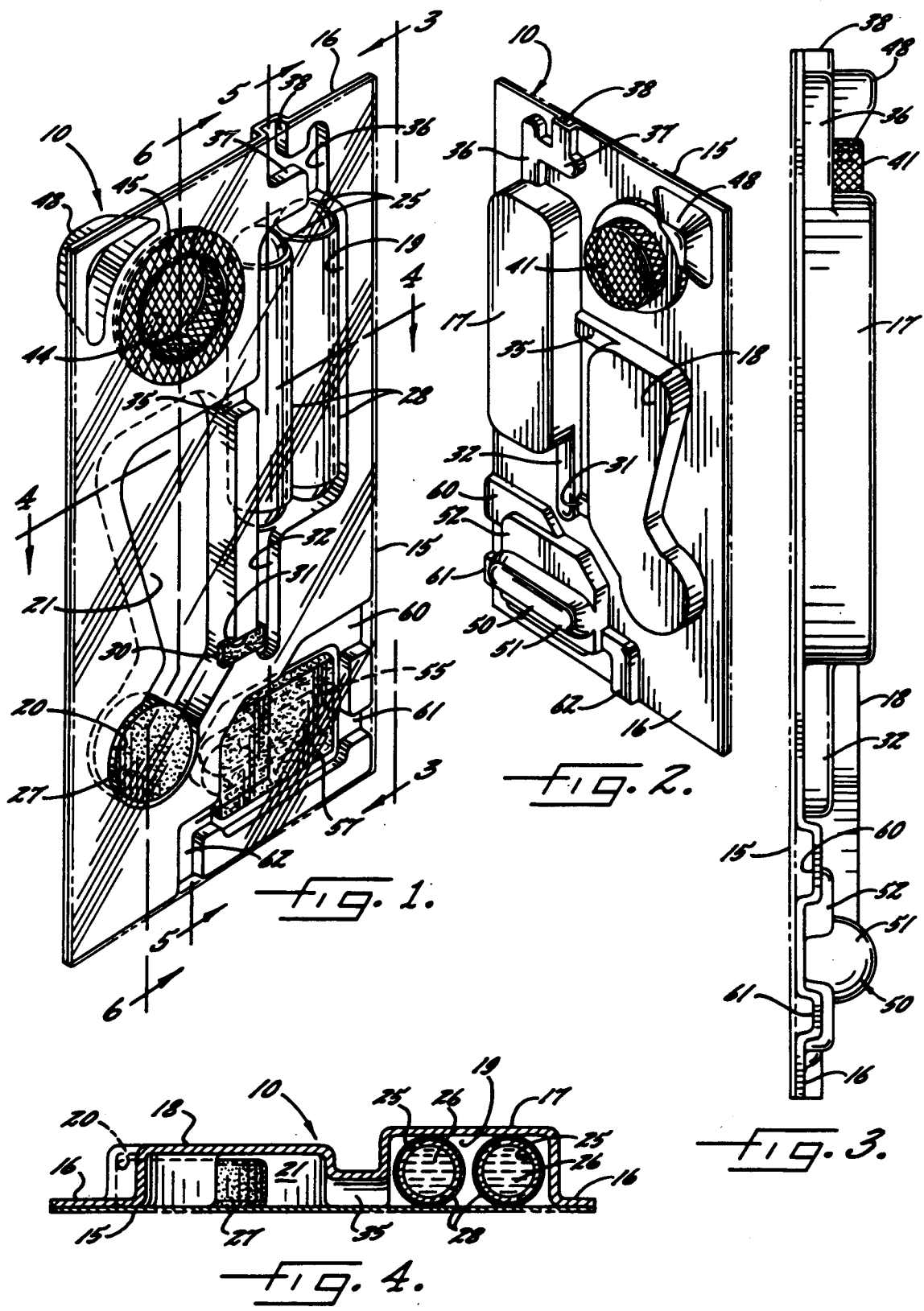

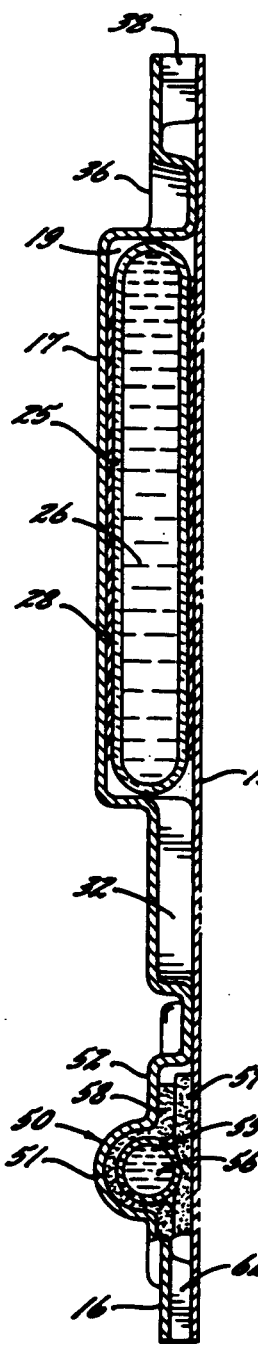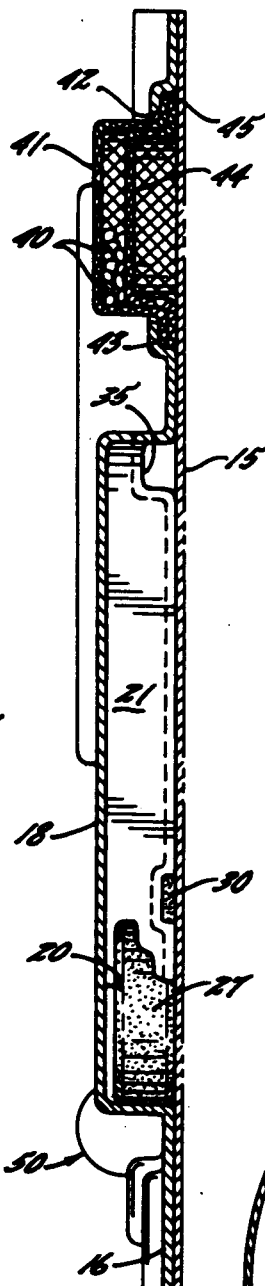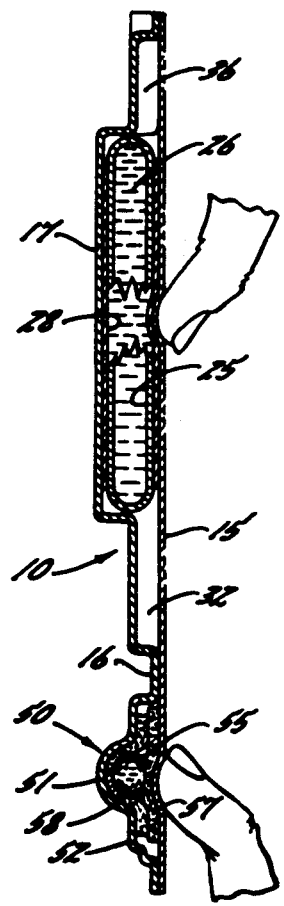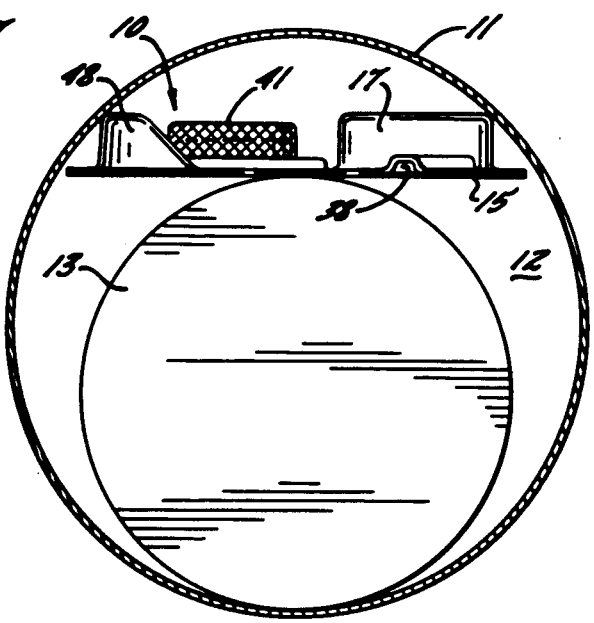

GAS GENERATOR/INDICATOR UNIT ADAPTED FOR USE IN AN UPRIGHT POSITION

BACKGROUND OF THE INVENTION

This invention relates to units for generating a predetermined gaseous atmosphere in a container and/or for indicating the presence or absence of the predetermined atmosphere in the container. More particularly, the invention relates to generating and/or indicating units for use by the medical profession in collecting and testing bacterial cultures of the type which remain viable only when in the presence of a particular gaseous environment or atmosphere. For example, bacteria of the anaerobic type require an oxygen-deficient or oxygen-free atmosphere and should be stored and incubated in an environment having little or no oxygen.

A unit which is used for the same general purpose as the unit of the present invention is disclosed in Avery U.S. Pat. No. 4,643,973. That unit comprises a relatively inexpensive bubble pack. One bubble of the pack houses an acid-containing ampoule and also houses tablets which generate hydrogen and carbon dioxide when activated by squeezing the bubble to crush the ampoule and release the acid. Gas flows from the bubble pack into the container to establish an anaerobic atmosphere in the container. The atmosphere of the container communicates with another bubble which houses an ampoule containing a color indicating liquid. When the latter ampoule is crushed, the liquid moistens an absorbent pad which changes colors as the atmosphere of the container changes from aerobic to anaerobic.

The unit disclosed in the aforementioned Avery patent is particularly adapted for use while disposed in a horizontal position and is usually placed along with the cultures or specimens in a sealed transport bag which then is placed in an incubating chamber. While this method of transporting and incubating the specimens is entirely satisfactory, the procedure which is followed in some laboratories is to place the specimens directly in a sealed chamber and to establish the anaerobic atmosphere in the chamber itself.

SUMMARY OF THE INVENTION

The general aim of the present invention is to provide a new and improved gas generating and/or indicator unit which, while being of relatively simple and inexpensive bubble pack construction, is particularly adapted for effective use in an upright position when placed directly in a sealed chamber.

Another object of the invention is to provide a bubble pack gas generating unit capable of being used in an upright position, capable of generating a relatively large volume of gas in a comparatively short period of time and capable of safe, convenient and effective operation.

A further object of the invention is to incorporate a reaction-promoting catalyst in the bubble pack itself and to position the catalyst in the pack in such a manner as to prevent heat evolved from the catalyst from damaging either the bubble pack or the chamber in which the pack is placed.

Another object is to provide a bubble pack gas generating and/or indicator unit in which passages for delivering gas from the generating unit and passages for admitting the atmosphere of the chamber to the indicating unit are formed in a simpler and less expensive manner than has been the case with prior units of the same general type.

These and other objects and advantages of the invention will become more apparent from the following detailed description when taken in conjunction with the accompanying drawings.

BRIEF DESCRIPTION OF THE DRAWINGS

FIG. 1 is a perspective view showing the back side of a new and improved gas generating/indicator unit incorporating the unique features of the present invention.

FIG. 2 is a perspective view showing the front side of the unit.

FIG. 3 is a side elevational view of the unit as seen along the line 3—3 of FIG. 1.

FIGS. 4, 5 and 6 are cross-sections taken substantially along the lines 4—4, 5—5 and 6—6, respectively, of FIG. 1.

FIG. 7 is a view generally similar to FIG. 5 but on a reduced scale and showing the ampoules of the unit being crushed.

FIG. 8 is a cross-sectional view taken radially through a chamber and showing the unit in an upright position in the chamber.

DETAILED DESCRIPTION OF THE PREFERRED EMBODIMENT

For purposes of illustration, the invention has been shown in the drawings in connection with a gas generating/indicator unit 10 of the type used with a system for incubating and testing bacterial cultures. While certain aspects of the invention are applicable for use with various incubating systems, the invention will be explained specifically in connection with a system which includes a cylindrical plastic container 11 (FIG. 8) having an inside diameter of about four inches and having a chamber 12 which defines an incubating chamber. Specimens to be tested are collected on plates or dishes 13 treated with a suitable growth media and sized to fit within the chamber 12. The dishes either are stacked on top of one another in the chamber or are stacked on a wire rack (not shown) which then is placed in the chamber. After the dishes have been placed in the chamber, an anaerobic or oxygen-free atmosphere is created in the chamber to promote growth of the specimens in the chamber.

The present invention contamplates the provision of a new and improved gas generating/indicating unit 10 which is in the form of a relatively simple, inexpensive and easy-to-use bubble pack and which is particularly adapted for use while oriented in an upright position in a chamber such as the chamber 12. The unit 10 is also characterized by its ability to quickly generate a relatively large volume of gas and by its safeguards against the risk of personal injury during use of the unit.

More specifically, the bubble pack unit 10 is of an elongated rectangular shape and includes a flat back panel 15 made of flexible and heat sealable material such as polypropylene having a thickness of about 0.010". Heat-sealed to the flat front side of the back panel is a front panel 16 whose front side is formed with a number of raised blisters or bubbles to be described subsequently. A suitable material for use as the front panel is talc-filled polypropylene having a thickness of about 0.025".

The bubble pack 10 is formed with two bubbles 17 and 18 defining compartments for holding materials for generating a gas. The bubble 17 is generally rectangular in shape and extends generally in the direction of elongation of the pack 10. Herein, the bubble 17 is primarily located in the upper half of the pack adjacent one side margin thereof and defines a compartment 19 (FIGS. 4 and 5).

As shown most clearly in FIG. 2, the bubble 18 is shaped somewhat like a boot and includes a lower generally cylindrical portion which defines a compartment 20 (FIG. 4). The upper end of the generally cylindrical compartment 20 communicates with an elongated compartment 21 (FIG. 6) which also is defined within the bubble 18. Upon progressing upwardly, the compartment 21 gradually widens as is apparent from the shape of the bubble 18 as shown in FIG. 2.

The bubble 18 is disposed alongside the bubble 17 and is positioned such that the cylindrical compartment 20 of the bubble 18 is located well below the compartment 19 of the bubble 17. The elongated compartment 21 of the bubble 18 terminates about midway along the height of the compartment 19.

Disposed in and extending longitudinally of the compartment 19 of the bubble 17 are two elongated sealed ampoules 25 (FIGS. 1, 4 and 5) made of glass or other frangible material, the ampoules substantially filling the compartment 19. Each ampoule contains a quantity (e.g. 2.5 ml.) of activating liquid 26 which herein includes phosphoric acid.

Located in and substantially filling the cylindrical compartment 20 of the bubble 18 is a gas generating material 27 (FIGS. 1, 4 and 6) in the form of a cylindrical tablet. In this instance, the tablet 27 consists of a mixture of potassium boro-hydride, sodium bicarbonate and zinc. Reaction of the acid 26 in the ampoules 25 with the tablet 27 generates a mixture of gases including hydrogen and carbon dioxide.

To generate the gases, the bubble 17 is squeezed to crush the ampoules 25 and release the acid 26 therein (see FIG. 7). Preferably, such crushing is effected by placing the pack 10 horizontally with the bubble 17 lying on a hard surface and by pushing downwardly on the flexible rear panel 15 in that area of the panel overlying the ampoules. Such pushing pinches the ampoules between the bubble 17 and the panel 15 and effects crushing of the glass ampoules. To prevent glass shards from the broken ampoules from penetrating the panel 15 and/or the bubble 17 during crushing of the ampoules, each ampoule is telescoped into a flexible cylindrical sleeve 28 (FIGS. 4 and 5) made of glycol-modified polyethylene terephthalate with a thickness of about 0.011". The sleeves are slightly elliptical in cross-section and are telescoped over the ampoules with a frictional fit.

In carrying out one aspect of the invention, the acid 26 released from the ampoules 25 is uniquely carried into the compartment 20 and into contact with the tablet 27 by a wick 30 (FIG. 1) which allows an adequate flow of acid into the compartment 20 while preventing such a fast flow as to result in a violent reaction with the tablet. The wick 30 is defined by a short length of absorbent material such as non-woven polyester and is fixed with a press fit in a horizontal passage or channel 31 (FIG. 2) which extends from the upper end portion of the compartment 20 of the bubble 18 to a vertical channel 32 leading from the lower end portion of the compartment 19 of the bubble 17. The channels 31 and 32 are defined between the panels 15 and 16 and are formed by depressing the rear side of the panel 16 forwardly during formation of the bubble pack 10. The channel 31 is significantly shallower than the channel 32 and, because of the wick 30, there is no need to hold close dimensional tolerances on the channel 31 either when the channel is formed or when the rear side of the channel is sealed by the rear panel 15. Even though the cross-sectional dimension of the channel 31 may not be precisely uniform from pack-to-pack, the wick 30 compensates for dimensional variances and allows the acid 26 to flow to the tablet 27 at a rate sufficiently fast to cause effective generation of the gas without causing a fast volcano-like reaction. In addition, the wick avoids the possibility of an air lock existing in the channel 31. By thickening the phosphoric acid with polyethylene glycol and propylene glycol, it is possible to eliminate the wick while still maintaining proper flow of the acid.

The gas generated by reaction of the acid 26 with the tablet 27 flows upwardly into the elongated or enlarged compartment 21 of the bubble 18. The compartment 21 serves as an overflow chamber for the released acid, the residue of the tablet, and foam resulting from the reaction of the acid with the tablet.

To further accommodate foam, a horizontal channel-shaped passage 35 (FIGS. 1 and 2) leads from the upper end of the compartment 21 to the compartment 19 about midway between the upper and lower ends of the latter compartment. Any excess foam may spill through the passage 35 and into the compartment 19. The passage 35 is formed in the same manner as the channel 31 but is substantially deeper than the channel.

Gas also flows through the passage 35 and into the compartment 19 of the bubble 17 and then flows out of the pack 10 and into the container 11 through passage means at the upper end portion of the pack. Advantageously, such passage means define a tortuous path in order to prevent acid droplets from flowing through the passage means and possibly causing injury when the ampoules 25 are broken. For this purpose, the passage means are defined by a vertical channel 36 (FIGS. 1 and 2) extending from the upper end of the compartment 19, a horizontal channel 37 communicating at one end with the upper end portion of the vertical channel, and a second vertical channel 38 communicating with the other end of the horizontal channel 37 and leading upwardly out of the pack 10. The channels 36, 37 and 38 are formed in the same manner as the channel 31 and define a labyrinth preventing acid from spewing directly out of the pack.

The hydrogen flowing out of the pack 10 mixes with the oxygen in the container 11 and the mixture interacts with a catalyst which herein is in the form of several palladium pellets 40 (FIG. 6). In the presence of the palladium pellets, the hydrogen reacts with the oxygen to form water and to reduce the surrounding atmosphere. As the gas mixture interacts with the pellets, the latter experience a significant rise in temperature.

In accordance with another feature of the invention, the catalyst pellets 40 are captivated in the pack 10 so as to enable a free flow of gas past the pellets while preventing the hot pellets from damaging either the plastic material of the pack or the material of the container 11. To these ends, the pellets are contained in a receptacle 41 which holds the pellets out in the chamber 12 of the container 11 while keeping the pellets away from the plastic of the pack. Specifically, the receptacle 41 is in the form of a dome made of aluminum wire mesh material and located so as to project from the front side of the pack. The dome 41 extends through a circular hole 42 (FIG. 6) in the panel 16 and its rear end is formed with a peripheral flange 43 which is captivated between the panels 15 and 16.

The pellets 40 are trapped near the front end of the dome 41 by a partition 44 (FIG. 6) which is disposed inside of the dome. Herein, the partition 44 also is in the form of a wire mesh dome which is slightly smaller than the dome 41 so as to be capable of fitting inside of the dome 41. The rear end of the dome 44 is formed with a peripheral flange 45 (FIGS. 1 and 6) which is sandwiched between the rear panel 16 and the flange 43 of the dome 41.

With the foregoing arrangement, the partition or dome 44 holds the pellets 40 closely adjacent the outer end of the outwardly projecting dome 41 so as to promote a free flow of the gas in the container 11 past the pellets. In addition, the dome 44 holds the pellets well away from the plastic rear panel 15 to prevent the hot pellets from melting through the panel.

Means are also provided for holding the outer end of the hot dome 41 out of contact with the inner side of the container 11. In this instance, these means comprise a generally triangular-shaped bubble 48 (FIGS. 1, 2, 3 and 8) which projects outwardly from the pack 10 adjacent the dome 41 and adjacent one upper corner of the pack. The bubble 48 projects from the pack approximately the same distance as the dome 41 and being located adjacent the corner of the pack, engages the inner wall of the container 11 and holds the dome 41 out of contact with the wall when the pack 10 is placed in an upright position in the container as shown in FIG. 8. The upper portion of the bubble 17 also engages the container wall and coacts with the bubble 48 to prevent the dome 41 from tilting into contact with the wall. Accordingly, the hot dome is held out of engagement with the container.

The bubble pack 10 is completed by an indicator for signaling whether or not oxygen has been effectively removed from the chamber 12 of the container 11 by the generated gases. For this purpose, the front side of the pack is formed with a bubble 50 (FIGS. 2 and 5) having an elongated front bubble portion 51 defining a compartment and a rear bubble portion 52 defining a compartment which communicates with the compartment defined by the bubble portion 51. The front bubble portion 51 is horizontal, is elongated transversely of the direction of elongation of the bubbles 17 and 18 and is positioned beneath the bubble 17 near the lower end portion of the pack 10. The rear bubble portion 52 is rectangular and is located behind the front bubble portion 51 in vertically centered relation therewith.

Disposed in the front portion 51 of the bubble 50 is an elongated sealed glass ampoule 55 (FIG. 5) containing a liquid 56, the liquid herein being a redox color indicating liquid such as 0.5 ml. of one percent resazurin. Located rearwardly of the ampoule 55 and disposed in the rectangular bubble portion 52 is a rectangular pad 57 of absorbent material such as white non-woven polyester. An additional pad 58 of white polyester encircles the front portion of the ampoule 55 and extends along the major length of that ampoule.

Unique passages 60, 61 and 62 (FIGS. 1 and 2) permit the atmosphere of the container 11 to enter the bubble 50. Advantageously, such passages are inexpensively formed and are defined between the panels 15 and 16. The passages 60 and 61 lead horizontally out of the upper and lower corners of the bubble portion 52 adjacent one margin of the pack 10 while the passage 62 leads out of the other lower corner of the bubble 50 and extends downwardly out of the pack. All three passages are formed simply by depressing the rear side of the panel 16 forwardly with appropriate die tooling during formation of the pack 10. This procedure is less expensive than coring air holes in the bubble portion 52. As a result of the three passages, the pads 57 and 58 are exposed to whatever atmosphere is present in the container 11.

Shortly before the ampoules 25 are crushed to generate the gas, the ampoule 55 is crushed by pressing the rear panel 15 against the ampoule 55 while the bubble portion 51 is resting against a rigid horizontal surface. The color indicating liquid 56 thus is released from the ampoule and moistens the pads 57 and 58, the pads preventing glass shards from penetrating the bubble 50 and the rear panel 15.

When the ampoule 55 is first crushed, oxygen is present in the container 11 and reacts with the color indicating liquid 56 soaked into the pads 57 and 58 to cause the pads to turn bluish-pink in color. After the ampoules 25 have been crushed and the gas starts to generate, the removal of oxygen from the container causes the pads to gradually fade back to their original white color. Accordingly, the medical technican can visually observe the color of the pads and determine whether an anaerobic atmosphere has in fact been created in the container. If the anaerobic condition is lost, the pads will return to their bluish-pink color to warn the technician that oxygen is present and that new cultures perhaps should be obtained.

From the foregoing, it will be apparent that the present invention brings to the art a new and improved gas generator/indicator unit 10 which is adapted to operate effectively in an upright position and whose components are housed within a single bubble pack. Following molding of the front panel 16 of the pack, the various components need merely be inserted into the appropriate bubbles and sealed therein by the rear panel 15. Such ease of manufacture and assembly lends itself to high speed and automatic techniques.

The unit 10 possesses a number of advantageous features including its ability to be used in an upright position; the provision of the wick 30 to achieve a controlled flow of acid 26 to the tablet 27; the domes 41 and 44 for permitting a free flow of gas past the catalyst pellets 40 while preventing the hot pellets from damaging the pack; and the coaction of the bubbles 17 and 48 to hold the hot dome 41 out of contact with the container 11. The passages 36, 37 and 38 reduce the danger of acid 26 spewing from the pack 10 during crushing of the ampoules 25 while the passages 60, 61 and 62 reduce the cost of molding the pack.

We claim:

1. A generator unit for creating a predetermined gaseous atmosphere in the environment immediately surrounding the unit, said unit comprising a bubble pack including a first panel having inner and outer sides, bubble means made of flexible material formed in said first panel and projecting from said outer side of said first panel, a gas generating material disposed in said bubble means, a sealed ampoule disposed in said bubble means and containing an activating liquid, a second panel made of flexible material sealed to said inner side of said first panel and captivating said gas generating material and said ampoule in said bubble means, said ampoule being fringible and being capable of being broken when said flexible material is manually flexed and squeezed against said ampoule, the released liquid reacting with said gas generating material to cause a gas to be generated in said bubble means, passage means formed in said inner side of said first panel and leading from said bubble means to the atmosphere surrounding said generator unit, said passage means defining a tortuous path for the gas to flow from said bubble pack and into the atmosphere surrounding said generator unit while preventing said liquid from escaping from said bubble pack and into the surrounding atmosphere, said passage means in said first panel being closed by said second panel except at locations where said passage means initially lead from said bubble means and finally lead to the atmosphere surrounding said generator unit, said tortuous path being defined entirely by said passage means in said first panel, and said bubble pack is adapted to be located in a generally vertical position during use, said bubble means comprising first and second bubbles disposed alongside one another and each having an upper end and a lower end, said ampoule being located in said first bubble, said gas generating material being located in the lower end portion of said second bubble, a channel for liquid defined between said first and second panels and extending from the lower end portion of said first bubble to the lower end portion of said second bubble for carrying said activating liquid to said gas generating material when said ampoule is broken, and a channel for gas extending between said bubbles above said liquid channel for carrying the gas from said second bubble to said first bubble, said passage means communicating with the upper end portion of said first bubble.

2. A generator unit as defined in claim 1 further including a wick made of absorbent material and disposed in said liquid channel to carry said activating liquid from said first bubble to said second bubble.

3. A generator unit for creating a predetermined gaseous atmosphere in the environment immediately surrounding the generator unit, said unit comprising a bubble pack including a first panel having first and second sides, bubble means made of flexible plastic material formed in and projecting from said first side of said first panel, a gas generating material disposed in said bubble means, a sealed ampoule disposed in said bubble means and containing an activating liquid, a second panel made of flexible plastic material sealed to said second side of said first panel and captivating said gas generating material and said ampoule in said bubble means, said ampoule being frangible and being capable of being broken when said flexible material is manually flexed and squeezed against said ampoule, the released liquid reacting with said gas generating material to cause a gas to be generated in said bubble means, passage means permitting the gas to escape from said bubble means and into the atmosphere surrounding said unit, a gas permeable receptacle connected to said bubble pack and projecting from said first side of said first panel, a catalyst in said receptacle for promoting a reaction between the gas and the surrounding atmosphere, and said receptacle is shaped as a hollow dome which projects from said first side of said first panel, said dome having a closed end, a partition within said dome and holding said catalyst near the closed end of said dome and in spaced relation with said second panel, said dome and said partition being made of a material having a higher melting point than said plastic material.

4. A unit as defined in claim 3 in which said partition is also shaped as a dome which fits inside of said first dome, each of said domes having a peripheral flange sandwiched between said panels.

* * * * *

UNITED STATES PATENT AND TRADEMARK OFFICE
CERTIFICATE OF CORRECTION

PATENT NO. : 5,057,285
DATED : October 15, 1991
INVENTOR(S) : Belt et al.

It is certified that error appears in the above-identified patent and that said Letters Patent is hereby corrected as shown below:

On the Title page item [73] Assignee: Marion Laboratories, Inc., Kansas City, MO"

Should read

Assignee: Becton, Dickinson and Company, Franklin Lakes, NJ--

Signed and Sealed this

Twenty-third Day of February, 1993

*Attest:*

STEPHEN G. KUNIN

*Attesting Officer*  *Acting Commissioner of Patents and Trademarks*